United States Patent [19]

Vrzalik

[11] Patent Number: 4,578,833

[45] Date of Patent: Apr. 1, 1986

[54] THERAPEUTIC OSCILLATING BED

[75] Inventor: John H. Vrzalik, San Antonio, Tex.

[73] Assignee: Kinetic Concepts, Inc., San Antonio, Tex.

[21] Appl. No.: 482,319

[22] Filed: Apr. 5, 1983

[51] Int. Cl.[4] .......................... A61G 7/00; A61G 7/06; A61F 5/37

[52] U.S. Cl. ........................................ 5/61; 128/80 R; 128/134; 5/109; 269/328

[58] Field of Search .............................. 128/33, 70–75, 128/80 R; 5/60–62, 81 R, 63–65; 269/322–328

[56] References Cited

U.S. PATENT DOCUMENTS

| | | | |
|---|---|---|---|
| 1,021,335 | 3/1912 | Robinson | 5/61 |
| 2,228,793 | 1/1941 | Swofford | 128/72 X |
| 2,667,169 | 1/1954 | Kambourakis | 5/60 X |
| 3,168,310 | 2/1965 | Strausser | 272/54 |
| 3,200,416 | 8/1965 | Warrick | 5/62 |
| 3,434,165 | 3/1969 | Keane | 128/71 |
| 3,732,584 | 5/1973 | James | 5/81 R |
| 3,840,265 | 10/1974 | Stirling et al. | 5/62 X |
| 4,010,499 | 3/1977 | Davis et al. | 5/81 R |
| 4,175,550 | 11/1979 | Leininger et al. | 5/61 X |
| 4,207,879 | 6/1980 | Safadago et al. | 128/70 |

OTHER PUBLICATIONS

"Super Tan", Feb. 11, 1981, *The Super Tan Tanning Lounge.*

*Primary Examiner*—Richard J. Johnson

*Attorney, Agent, or Firm*—Cox & Smith Inc.

[57] ABSTRACT

An oscillating hospital bed having an oscillating frame for oscillating about a longitudinally extending axis and a patient support mounted on the oscillating frame for controlled pivoting of the patient support about a transverse axis. Securing devices are provided on the patient support to hold a patient in place and the oscillating frame is cantilevered from a base support.

17 Claims, 4 Drawing Figures

THERAPEUTIC OSCILLATING BED

BACKGROUND OF THE INVENTION

This invention relates to therapeutic beds and more particularly to hospital beds for use by immobilized patients. In particular the invention relates to hospital beds for use by patients who are partially or fully paralyzed, suffering from head injuries, having multiple sclerosis, fractured spines or similar serious injury, to render the patient temporarily or permanently immobile.

The use of oscillating hospital beds is known in the prior art. A pioneer invention in this field is U.S. Pat. No. 3,434,165 issued to F. X. Keane. The Keane bed has been made in regular sizes which are not always suitable for very small patients and for children's or pediatric units.

An object of the present invention is to provide a children's or pediatric oscillating hospital bed using the same principles of U.S. Pat. No. 3,434,165 and suitable for use for smaller or pediatric patients. It is a further object of the invention to provide a pediatric oscillating hospital bed which can be used in conjunction with conventional treatment methods and apparatus for pediatric patients and which can be used in conventional pediatric intensive care units and with smaller patients. It is a further object of the invention to provide a cantilevered oscillating hospital bed having a removable patient supporting portion for ease of access and transport of a patient on the oscillating hospital bed.

Another oscillating hospital bed is disclosed in U.S. Pat. No. 4,175,550 issued to James R. Leininger et al and which is commonly assigned to the assignee of the present application. Another example of an oscillating hospital bed is copending application Ser. No. 226,118 filed Jan. 19, 1981, which has the same inventor as this application and is also commonly assigned. U.S. Pat. No. 3,434,165, U.S. Pat. No. 4,175,550 and application Ser. No. 226,118 filed Jan. 19, 1981, are incorporated herein by specific reference for all purposes.

SUMMARY OF THE INVENTION

The invention comprises an oscillating therapeutic hospital bed apparatus having a base support means, an oscillating frame means, a power motor drive means, a patient supporting means and pack means. The cantilevered oscillating frame means is pivotably mounted about a horizontal longitudinally extending pivot axis. The patient supporting means is pivotably mounted for head to foot tipping movement of a patient thereon about a transverse axis relative to the oscillating frame means. The oscillating frame means is cantilevered about a single pivot axis at one end. The patient supporting means can be removed from the oscillating frame means for transport of a patient thereon.

DETAILED DESCRIPTION OF THE PREFERRED EMBODIMENT

Figure 1:
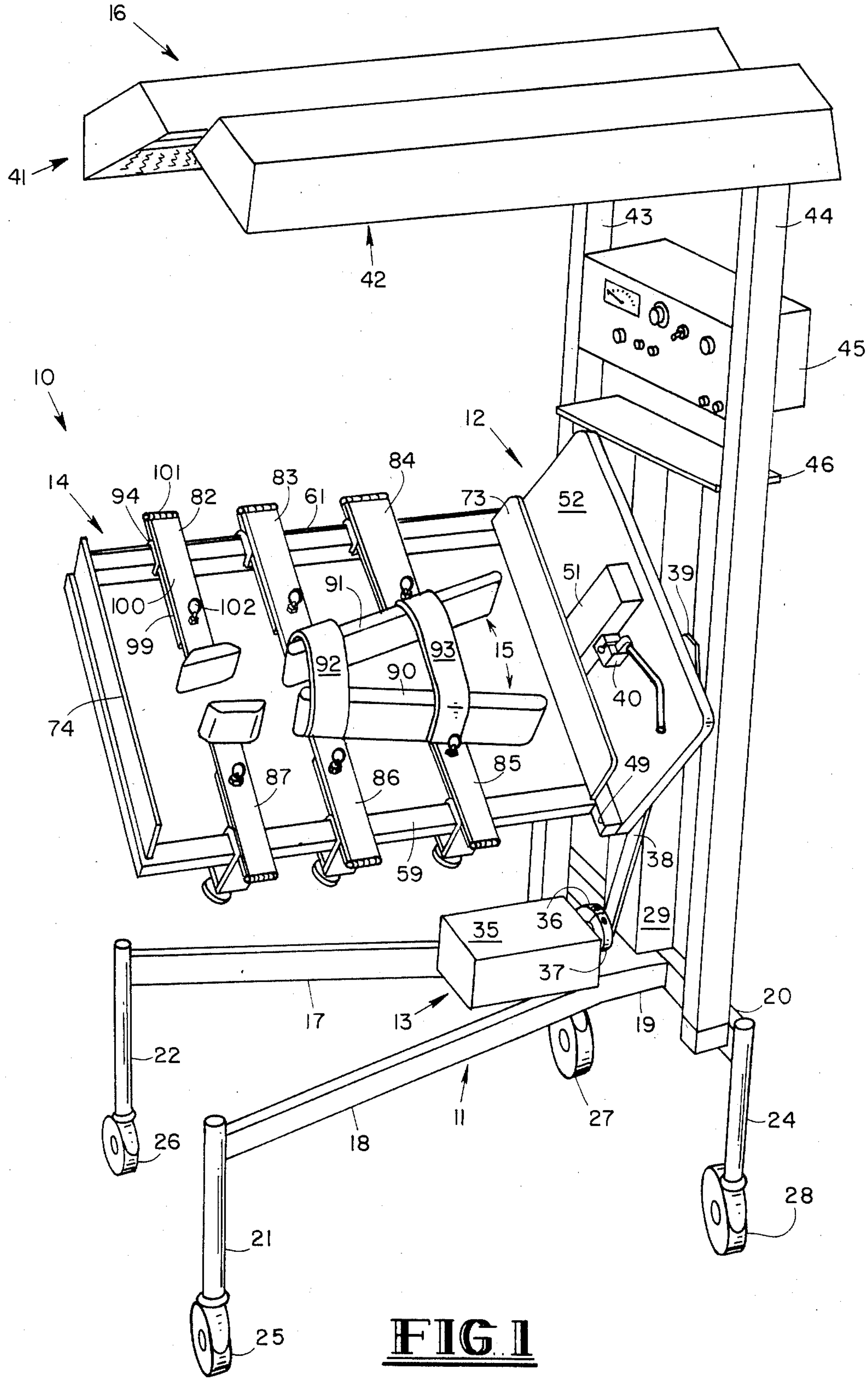
FIG. 1 is a perspective view of an oscillating therapeutic bed according to the invention.

Referring to FIG. 1 of the drawing, there is shown an oscillating therapeutic bed 10. The bed includes a base support means 11 to which is pivotably connected a cantilevered oscillating frame means 12. A motor drive means 13 oscillates the frame means 12 to provide controlled oscillatory movement. A patient support means 14 is mounted upon the oscillating frame means 12 for supporting the patient thereon. A pack means 15 maintains the patient in position on the patient support means during the oscillation. A heater means 16 may also be provided to maintain body temperature.

The base support means 11 includes a plurality of horizontal frame members 17 and 18 which are joined together through connecting member 19 which is secured to horizontal cross member 20. Vertical leg posts 21 and 22 are secured to the horizontal leg members 18 and 17 respectively. The vertical leg posts 23 and 24 are secured to opposite ends of the horizontal cross member 20. Roller wheels 25, 26, 27 and 28 are secured to the lower ends of vertical leg posts 21, 22, 23 and 24 respectively.

A vertical support post 29 is secured to the connecting member 19 and horizontal cross member 20. The vertical support post 29 includes a journal housing and bearing 30 which rotatably supports a pivot axis 31. The journal housing and bearing member 30 forms a first longitudinally extending pivot means and the pivot axis 31 forms a second longitudinally extending pivot means.

A locking pin 32 is slidably mounted in housing 32' which is secured to the vertical support post 29. Locking knob 33 is connected to the locking pin 32 whereby the locking pin may be reciprocated into and out of a plurality of slots in arcuate locking member 34 which is connected to the oscillating frame means 12. An electrical switch may be provided in housing 32' so that when the locking pin 32 extends into an aperture in the arcuate member 34 the motor drive means 13 is disconnected from the power source so that the bed will not oscillate.

The motor means 13 includes an electric motor which is covered by the housing 35. The electric motor includes a gear reduction unit which has an output drive shaft 36 which is connected to a slip clutch means 37. The slip clutch includes a central disc mounted on the output shaft. Two semi-circular outer sections are releasably clamped around the periphery of the disc and the amount of clamping force determines the slipping point. A plastic strip may be positioned between the disc and two outer sections to facilitate slippage. A pin eccentrically mounted on one of the outer sections is rotatably connected to lever 38. Eccentrically connected with the slip clutch means 37 is a reciprocating lever 38. At the end of the reciprocating lever 38 there is a releasable connecting means 39 which is connected by a lever to the variable oscillation means 40. Rotation of the drive shaft 36 and slip clutch 37 causes the reciprocating lever 38 to reciprocate which in turn oscillates the oscillating frame means 12. The releasable connecting means 39 connects the reciprocating lever 38 to the oscillating frame means 12. The variable oscillating means 40 permits varying of the degree of oscillation of the bed. The motor drive means 13 is more fully shown in pending application Ser. No. 226,118 filed Jan. 19, 1981, which is incorporated herein by reference. The motor drive means will oscillate the oscillating frame means at least 45 degrees in each direction to provide the necessary motion to a patient to maintain body functions and prevent bedsores.

Figure 3:
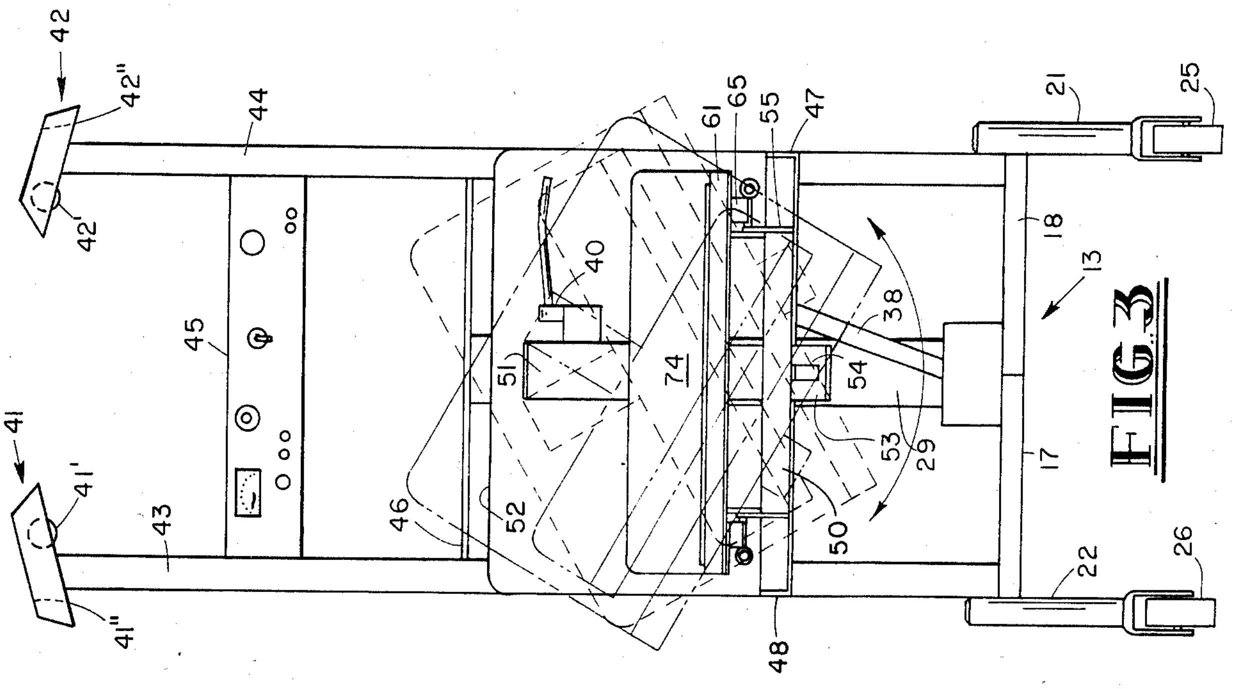
FIG. 3 is a front elevation view of the therapeutic hospital bed showing the oscillating movement in broken lines.

A heater means 16 may also be provided for use with the oscillating bed. The heater means shown may include two heaters 41 and 42 which are oriented at an angle as shown in FIG. 3. Heaters 41 and 42 include a heating element 41' and 42' with a reflector 41'' and reflector 42''. The orientation and shape of the reflectors 41'' and 42'' is such that relatively even heating is provided to a patient on the patient support means 14 during the oscillatory movement which is shown in broken lines in FIG. 3. Without this type of arrangement the heating may not be uniform as the patient oscillates which is not desired. The heating elements must cover a relatively broad range with the heat being distributed over a broad area of the patient support means 14 to provide the even heating. Vertical supports 43 and 44 are connected to the horizontal cross mebmer 20 to hold the heaters 41 and 42. A control panel 45 is provided to regulate the heaters. A shelf member 46 is connected to the upper portion of the vertical support post 29 and to the vertical supports 43 and 44.

The oscillating frame means 12 is cantilevered in that it is supported at only one end; it includes longitudinally extending beam members 47 and 48 which are connected by transversely extending cross members 49 and 50 to form a frame. The cross member 49 is connected to an upper vertical post portion 51 which is in turn connected to the pivot axis 31. A headboard 52 is also connected to the upper vertical post portion 51. A lower vertical post portion 53 is also connected to the cross member 49 and a centrally located and longitudinally extending reinforcing beam 54 is connected to the post portion 53 and cross member 50.

Figure 2:
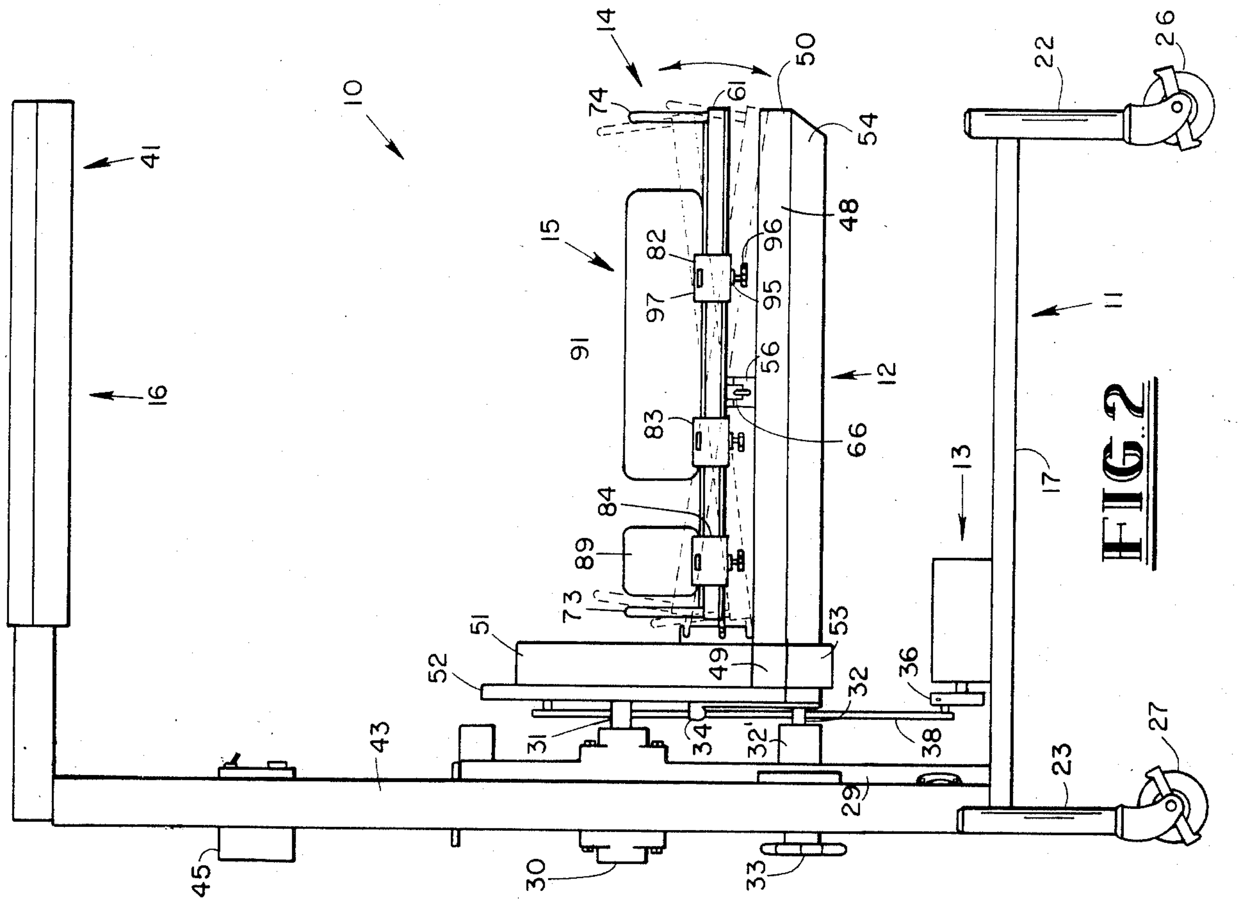
FIG. 2 is a side elevation view of the therapeutic hospital bed.

A transverse pivot support 55 having a transverse pivot aperture thereon is connected to the beam 47 and another transverse pivot support 56 having a transverse pivot aperture thereon is connected to the beam to support the patient support means 14. A transverse pivot latch 57 having a plurality of locking notches therein is also connected to the beam 47 and a transverse pivot latch 58 having locking notches is connected to the beam 48. The patient support means 14 is pivotably connected to the pivot supports 55 and 56 and is maintained in position as shown in FIG. 2. The patient support means 14 may be rocked or tipped head to foot or maintained in a horizontal position.

Figure 4:
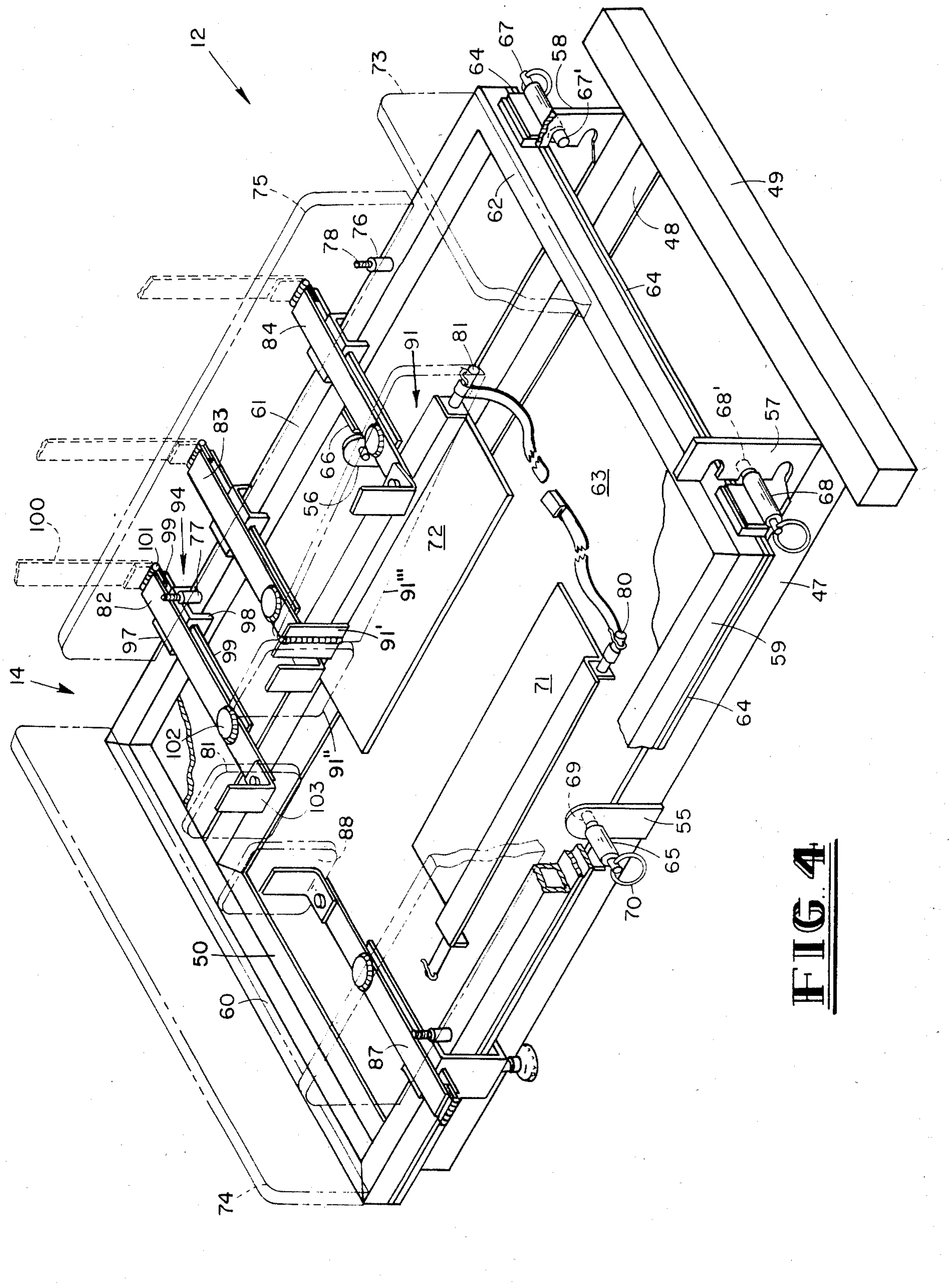
FIG. 4 is a partial view showing the oscillating frame means and patient support means with portions broken away to show the mechanism.

The patient support means 14 is specifically shown in FIG. 4. It includes a generally rectangular frame including beam members 59, 60, 61 and 62. A glass or plastic base sheet 63 is secured to the lower surfaces of the members 59, 60, 61 and 62 with a suitable fastener such as rivets or screws. Flat edge protector strips 64 are provided to prevent chipping of the edge of the base sheet. Since the base sheet 63 is secured to the lower surface of the members 59, 60, 61 and 62 a recess is formed in which a mattress of foam material covered with a plastic covering which is usually staph checked is inserted.

Reciprocating pull latch means 65, 66, 67 and 68 are provided for mounting the patient support means onto the oscillating frame means. Each latch means is identical and includes a reciprocating pin such as pin 69 which inserts in an aperture such as in the transverse pivot support 65. By pulling on the ring 70, the pin 69 is retracted against a coil spring inside the latch means so that the pin is removed from the aperture. In the case of the latch means 67 and 68 this enables their respective pins 67' and 68' to be retracted from a selected notch in the transverse pivot latches 58 and 57 so that the patient support means may be rocked or tipped from head to foot as desired. In order to remove the patient support means from the oscillating frame means one need only release the latch means 65 and 66 as indicated above from the transverse pivot supports 55 and 56 so that the patient support means may be lifted off of the oscillating frame means.

Secured to the bottom of the base sheet 63 by rivets or bolts are X-ray supports 71 and 72. A sheet of X-ray film may be positioned in the X-ray supports 71 and 72 for X-raying a patient. End members 73 and 74 may be releasably secured to the members 62 and 60 respectively. If desired, a side member such as side member 75 may be used. The side member 75 may be releasably mounted to each of the members such as member 61 by securing cylindrical holders 76 and 77 to a side member such as 61 and having pin members 78 and 79 secured to the side members 75 and positioned to be slidably inserted in the tubular members 76 and 77 to detachably secure the side member 75 in place. Rod members 80 and 81 are secured to apertures on the X-ray supports 71 and 72. Suitable nylon straps may be secured to the rod members so that they may be extended over a patient lying on the patient supporting platform to maintain the patient in place. These may in the form of conventional nylon strapping material with a releasable and adjustable catch.

Suitable pack means are releasably and adjustably mounted upon the patient support means to retain a patient thereon during the oscillation. Each of the adjusting brackets for the pack means is identical. As shown in FIG. 1, the pack support bracket means 82, 83, 84, 85, 86 and 87 releasably and adjustably maintain varying sized patients on the patient supporting platform. A patient's head is positioned between the head packs 88 and 89. The patient's body is positioned between the packs 90 and 91, which are mirror images of each other, with only the arms extending outwardly from the packs. The packs 90 and 91 are hinged as shown in FIG. 4 where internal hinge 91' is shown. The arm portion 91'' of the side pack 91 is connected to the bracket 83 and remains parallel while the leg portion 91''' may be pivoted outwardly. Flexible straps 92 and 93 are provided to help retain the patient between the side packs 90 and 91. These straps may be made of flexible or cushioned plastic material and are releasably connected to the side packs 90 and 91 with hook and loop fasteners so that they may be removed to place a patient on the bed or remove a patient from the bed.

Each of the pack support brackets is the same so a description will only be given of bracket 82. The pack support bracket 82 includes a pack clamp member 94 which is generally C-shaped. The lower leg 95 of the clamp is horizontal and includes a threaded aperture therethrough which receives hand screw 96 which is positioned to engage the lower surface of the flat strip 64. The upper leg portion 97 includes a horizontal and vertical portion 98 which wraps around the member 61 to retain it in position. When the hand screw 96 is tightened it engages the lower surface of strip 64 on the base sheet 63 to tightly clamp the upper leg portion 97 in engagement with the upper surface portion of the member 61. When the hand screw 96 is loosened, it allows the pack clamp member 94 to be longitudinally slidably secured to a selected location along the member 61. Strap member 99 extends through rectangular and transversely spaced openings in the pack clamp member and is positioned between the upper leg 97 of the pack clamp member and the upper surface of the member 61. Accordingly, when the hand screw 96 is tightened, it also clamps the strap member 99 in position. When the hand screw 96 is loosened, it permits transverse reciprocation of the strap member 99 inwardly or outwardly so that the packs may be adjusted laterally to accommodate different sized patients. A second strap member 100 is pivotably connected to the strap member 99 by hinge 101. A quarter turn fastener or a screw 102 extends through the strap member 100 and releasably engages a receptacle or threaded portion in the strap member 99 to normally retain the strap member 100 in its position shown in solid lines in FIGS. 1, 2 and 4. Rotation of the fastener 102 disengages it from the threaded portion on strap 99 so that the strap 100 may be pivoted upwardly out of the way for access to the patient as shown in broken lines in FIG. 4. An L-shaped swivel bracket 103 is connected to the strap 100 by suitable means such as a rivet or bolt and has a leg which is connected to one of the pack means to support it in its vertical position. Suitable padding may be provided on top of strap member 100 so as to cushion the strap member 100 against contact by a patient or someone treating the patient on the bed. L-shaped swivel brackets are used on bracket means 82, 84, 85 and 87 to allow pivoting movement of the pack portions connected thereto. The L-shaped vertical portions on bracket means 83 and 86 cannot be swiveled.

In order to position a person on the bed, the patient support means is positioned in its horizontal position as shown in FIG. 2. Each hand screw on each of the pack clamp members is loosened so that the packs may be adjusted longitudinally and transversely to allow positioning of a patient. The flexible straps 92 and 93 are removed so that a patient may be positioned between the side packs 90 and 91. When the patient is positioned between the side packs 90 and 91 and the head packs 88 and 89, the packs are then adjusted so that they comfortably rest against the patient to retain a patient in position and prevent undesired movement during oscillation of the patient. The flexible straps 92 and 93 are placed in position and if desired restraining straps connected to the rods 80 and 81 are looped over the bed and connected to each other to further retain the patient in position and prevent movement. Typically three such restraining straps may be used. The drive motor means 13 is then activated to provide oscillation of the patient.

Although the invention has been described in conjunction with the foregoing specific embodiment, many alternatives, variations and modifications will be apparent to those of ordinary skill in the art. Those alternatives and modifications are intended to fall within the spirit and scope of the appended claims.

I claim:

1. An oscillating therapeutic bed apparatus comprising:

a base support means having a generally vertical support post and a first longitudinally extending pivot means mounted on the generally vertical support post;

an oscillating frame means having a second longitudinally extending pivot means connected to the first longitudinally extending pivot means to cantilever the oscillating frame means to the generally vertical support post for controlled oscillatory movement of the oscillating frame means about a longitudinally extending horizontal axis relative to the base support means;

a motor drive means to provide a controlled oscillatory movement of the oscillating frame means relative to the base support means;

a patient support means pivotably mounted on the oscillating frame means intermediate its ends by a transverse pivot axis means for controlled pivoting of the patient support means about the transverse pivot axis means relative to the oscillating frame means so that the transverse pivot axis means oscillates with the patient support means, the longitudinally extending horizontal axis about which the oscillating frame means oscillates remaining generally horizontal relative to the base support means during controlled pivoting of the patient support means;

the transverse pivot axis means including a releasable pivot means so that the patient support means may be removed from the oscillating frame means and latching means to selectively latch the patient support means from transverse pivoting; and pack means on the patient supporting means including transversely and laterally adjustable head and body packs to restrain a patient's head and body to protect and maintain a patient on the patient supporting means during oscillatory movement and restraining strap means to restrain a patient on the patient support means.

2. The apparatus as set forth in claim 1, wherein:

the pack means is hinged about a longitudinal axis to pivot it out of the way for positioning and access to a patient on the patient support means.

3. An oscillating therapeutic bed apparatus comprising:

a base support means having a first longitudinally extending pivot means;

an oscillating frame means having a second longitudinally extending pivot means connected at one end to the first longitudinally extended pivot means of the base support means for controlled oscillatory movement of the oscillating frame means about a longitudinally extending horizontal axis relative to the base support means;

a motor drive means to provide controlled oscillatory movement of the oscillating frame means;

a patient support means pviotally mounted intermediate its ends on the oscillating frame means by a transverse pivot axis means for controlled pivoting of the patient support means about the transverse pivot axis means relative to the oscillating frame means so that the transverse pivot axis means oscillates with the patient support means, the patient support means having a generally vertical support post and the oscillating frame means being cantilevered at one end from the generally vertical support post on the first longitudinally extending pivot means; and pack means on the patient support means to protect and maintain a patient thereon during oscillatory movement.

4. The apparatus as set forth in claim 3, wherein:

the transverse pivot axis means includes releasable pivot means so the patient support means may be removed from the oscillating frame means.

5. The apparatus as set forth in claim 4, wherein: the releasable pivot means are laterally spaced at each side of the patient support means.

6. The apparatus as set forth in claim 3, wherein: the transverse pivot axis means includes latching means to selectively latch the patient support means from transverse pivoting.

7. The apparatus as set forth in claim 6, wherein: the latching means has vertically positioned slots and pin means selectively positioned in a slot to position the patient support means.

8. The apparatus as set forth in claim 3, wherein: heater means are provided to maintain uniform temperature of a patient on the patient support means during oscillation.

9. The apparatus as set forth in claim 8, wherein: the heater means includes two lateral radiant heaters positioned above the patient support means to provide the uniform temperature.

10. The apparatus as set forth in claim 3, wherein: the pack means includes transversely and laterally adjustable head packs to restrain a patient's head during oscillation.

11. The apparatus as set forth in claim 10, wherein: the head packs are hinged about a longitudinal pivot axis to pivot it out of the way for positioning and access to a patient on the patient support means.

12. The apparatus as set forth in claim 3, wherein: the pack means includes transversely and laterally adjustable side packs to restrain a patient's body during oscillation.

13. The apparatus as set forth in claim 12, wherein: the side packs are hinged about a longitudinal pivot axis to pivot it out of the way for positioning and access to a patient on the patient support means.

14. The apparatus as set forth in claim 3, wherein: the packs means includes transversely and laterally adjustable head and side packs to restrain a patient's head and body during oscillation.

15. The apparatus as set forth in claim 14, wherein: the head and side packs are hinged about a longitudinal pivot axis for swinging out of the way for positioning a patient and access to a patient on the patient support means.

16. The apparatus as set forth in claim 3, wherein: the pack means includes restraining strap means to restrain a patient on the patient support means.

17. The apparatus as set forth in claim 3, wherein: the pack means is hinged about a longitudinal axis to pivot it out of the way for positioning and access to a patient on the patient support means.

* * * * *